United States Patent [19]

Nottingham et al.

[11] Patent Number: 4,803,638
[45] Date of Patent: Feb. 7, 1989

[54] ULTRASONIC SIGNAL PROCESSING SYSTEM INCLUDING A FLAW GATE

[75] Inventors: Lawrence D. Nottingham, Charlotte, N.C.; Thomas E. Michaels; Jennifer E. Michaels, both of Freeville, N.Y.

[73] Assignee: Westinghouse Electric Corp., Pittsburgh, Pa.

[21] Appl. No.: 878,817

[22] Filed: Jun. 26, 1986

[51] Int. Cl.⁴ ............................................. G01N 29/04
[52] U.S. Cl. ..................................... 364/507; 73/596
[58] Field of Search ............... 364/507, 502; 73/607, 73/611, 612, 615, 628, 596; 128/660

[56] References Cited

U.S. PATENT DOCUMENTS

| | | | |
|---|---|---|---|
| 3,221,544 | 4/1965 | Gunkel | 73/626 |
| 3,415,110 | 1/1970 | Cowan | 73/609 |
| 3,575,044 | 4/1971 | Gibbs | 73/612 |
| 3,583,211 | 6/1971 | Brech | 73/67.8 |
| 3,920,970 | 11/1975 | Slaker | 356/430 |
| 3,996,792 | 12/1976 | Kubota et al. | 364/507 |
| 4,074,564 | 2/1978 | Anderson | 364/414 |
| 4,213,183 | 7/1980 | Barron et al. | 364/487 |
| 4,229,796 | 8/1980 | Garrett | 364/507 |
| 4,252,024 | 2/1981 | Hurwitz | 367/8 |
| 4,380,172 | 4/1983 | Imam et al. | 364/507 |
| 4,428,237 | 1/1984 | Zeger et al. | 73/592 |
| 4,660,419 | 4/1987 | Derkacs et al. | 73/622 |

FOREIGN PATENT DOCUMENTS

85/05683 12/1985 PCT Int'l Appl. .................. 364/507
664763 1/1952 United Kingdom .

Primary Examiner—Parshotam S. Lall
Assistant Examiner—Ellis B. Ramirez
Attorney, Agent, or Firm—D. C. Abeles

[57] ABSTRACT

An ultrasonic signal processing system that includes flaw gates that process signals from an inspection transducer is disclosed. The flaw gates operate in pairs where each pair is dedicated to a time window corresponding to, for example, flaw depth or transducer angle. The time window for a pair of flaw gates is indicated by a channel code produced by a timing control unit. One flaw gate in each pair processes incoming digitized transducer signals during a scan to produce reflector indications while the other gate in each pair transfers data from a previous different position scan to a main computer. The main computer determines flaw locations from the reflector indications and transducer positions provided by the flaw gate. The flaw gates each adjust reflector indication location signals for changes in distance between an immersed ultrasonic wave inspection transducer and the surface of the material being inspected as well as record the location of the inspection transducer at the time of each indication detection. The flaw gates produce the indication by comparing the digitized transducer signal waveform with a threshold curve where an indication is an excursion of the signal waveform above the threshold. The flaw gates each contain a comparator that indicates when the window is open and activates a waveform memory that automatically stores the digitized transducer signals during the window.

13 Claims, 14 Drawing Sheets

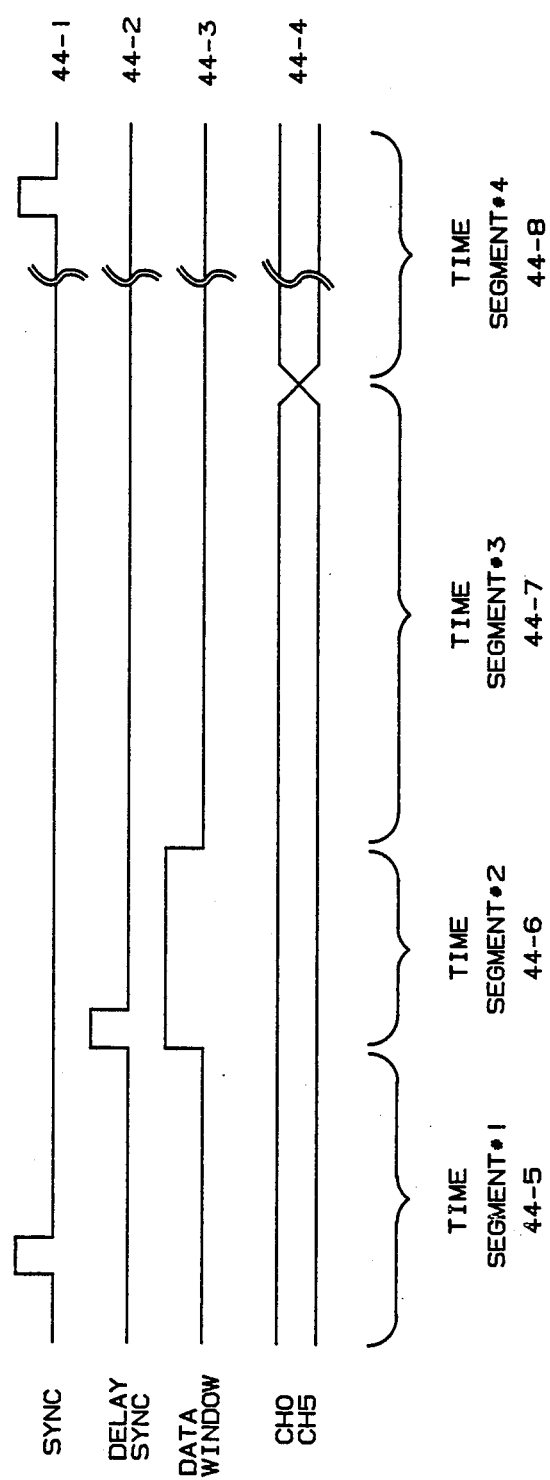

ULTRASONIC SIGNAL PROCESSING SYSTEM INCLUDING A FLAW GATE

CROSS REFERENCES TO RELATED APPLICATIONS

The present invention is related to concurrently filed U.S. application Ser. No. 878,649 assigned to Westinghouse entitled BORE MAPPING AND SURFACE TIME MEASUREMENT SYSTEM and allowed U.S. application Ser. No. 117,918 entitled BORESONIC INSPECTION SYSTEM. Both of the above-mentioned U.S. patent applications are incorporated by reference herein.

BACKGROUND OF THE INVENTION

The present invention is directed to a high speed ultrasonic signal processing system that captures all of the ultrasonic signals necessary for an ultrasonic inspection and, more particularly, to a system that uses paired flaw gates where each flaw gate processes data during a time window that corresponds to depth within the material being inspected and the data collected by one of the flaw gates in the pair is transferred to a central control and flaw location computer while the other flaw gate in the pair processes incoming ultrasonic signal data.

In a computerized ultrasonic inspection system, in general, the limitations on incoming signal processing speed also limit the speed at which an inspection of an object such as a power plant turbine rotor can be conducted. Volumetric ultrasonic inspections must sweep an ultrasonic beam through the entirety of the material being inspected to obtain complete coverage. If the size of the flaws to be detected is very small, a small ultrasonic beam is required involving a substantial number of beam passes through the material to detect all the flaws. The total time required for an inspection is a major factor in the cost of examining objects such as turbine rotor bores. Inspection of turbine rotor bores at the end of the manufacturing process as well as during periodic routine maintenance is required to detect flaws near the bore surface that can be removed by remachining or to detect deeper flaws that must be monitored to determine their changes so that the rotor can be removed from service before a catastrophic failure occurs. Reduced inspection time is thus particularly desired by power generating utilities.

A significant factor which limits the speed of rotor inspection is the time required to record the data associated with ultrasonic indications which when found can indicate a flaw. An ultrasonic indication is a reflection signal received by a transducer which exceeds an amplitude threshold level established during a calibration procedure. A flaw gate is used to establish the minimum and maximum transit time intervals between which data will be processed as well as to compare the return signal data to the amplitude threshold. A conventional flaw gate is essentially a windowed threshold comparator used on a returning echo signal which allows only ultrasonic indication signals to pass through for further processing. The signal is passed when it is within the time window and exceeds the amplitude threshold. For each indication it is necessary separately to record the amplitude of the indication, the time of flight of the pulse producing the indication and the position coordinates of the transducer within the rotor reference frame at the time the indication is detected. When the above data are combined with knowledge concerning the path geometry of the ultrasonic beam, the location of the reflector or flaw as well as its size can be determined.

In conventional computer operated ultrasonic inspection systems the computer must read not only the status of the ultrasonic instrumentation devices but also the position of the transducer. If an indication is recorded, the single computer stores a record of the time of the indication along with the scanner position. This conventional scheme becomes highly inaccurate and data may be missed if the scan speed is so rapid that the main computer is not able to keep up wth the rate at which data comes from the transducer.

SUMMARY OF THE INVENTION

It is an object of the present invention to provide a high speed ultrasonic signal processing system that collects ultrasonic indications.

It is another object of the present invention to provide approximate real time signal processing in a flaw gate to reduce workload on a main computer system which determines flaw location and size from flaw indications provided by the flaw gate.

It is a further object of the present invention to provide a flaw gate capable of not only transferring flaw indication data to the main computer but also collection of and processing of same.

It is another object of the present invention to provide paired flaw gates allowing one gate to process data while the other transfers previously collected and processed data to the main computer thereby preventing loss of transducer data and speeding up the inspection process.

It is an additional object of the present invention to provide plural pairs of flaw gates where each pair processes data within a transit time window corresponding to flaw depth, focal zone or transducer position.

It is yet another object of the present invention to provide a flaw gate that can correct for system perturbations such as in the surface time required for the inspection transducer beam pulse to reach the surface of the material being inspected.

It is a further object of the present invention to provide a flaw gate which is suitable for shear mode ultrasonic inspection.

The above objects can be attained by an ultrasonic signal processing system that includes flaw gates having signal processing capability. The flaw gates operate in pairs where each pair is dedicated to a transit time window corresponding to, for example, flaw depth. One flaw gate in each pair processes incoming digitized transducer signals while the other gate in each pair transfers previously processed data to a main computer that determines flaw locations from the reflector indications and the transducer positions both provided by the flaw gate. The flaw gates adjust reflector indication location signals for changes in distance between an immersed inspection transducer and the surface of the material being inspected as well as record the location of the inspection transducer at the time of each indication detection.

These together with other objects and advantages which will be subsequently apparent, reside in the details of construction and operation as more fully hereinafter described and claimed, reference being had to the accompanying drawings, forming a part hereof, wherein like numerals refer to like parts throughout.

BRIEF DESCRIPTION OF THE DRAWINGS

FIGS. 2B and 2C are timing diagrams of the data and control bus 30 signals and the outputs of the state counter 54 in FIG. 2A;

DESCRIPTION OF THE PREFERRED EMBODIMENTS

Figure 1:
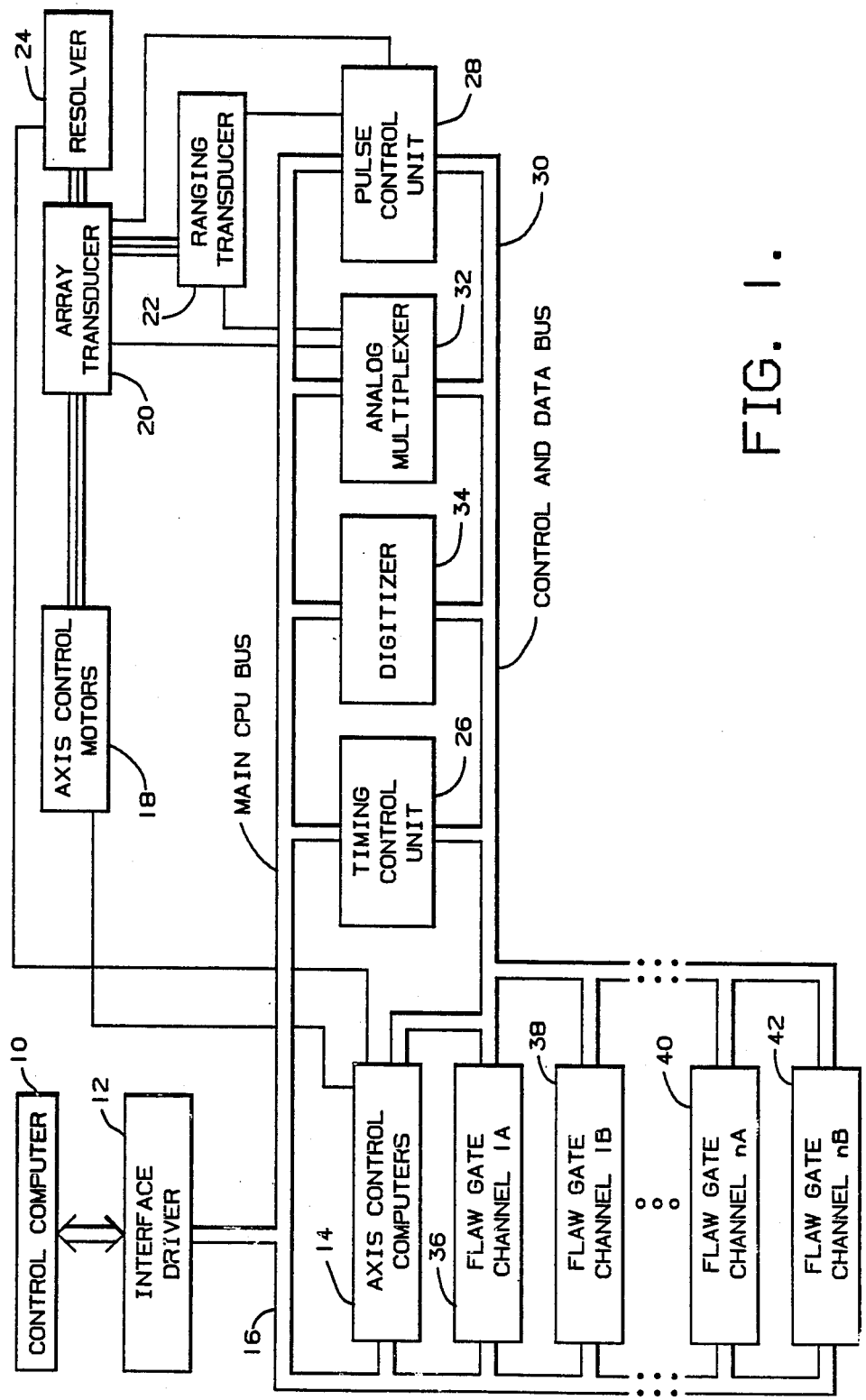
FIG. 1 is a block diagram of the components of the present invention.

The present invention allows high speed ultrasonic inspection of an object, such as a power generating plant turbine rotor, using a rapidly moving shear mode scanning mechanism without introducing positional error and without losing data. The system of the present invention allows costs associated with ultrasonic rotor inspection time to be significantly reduced. In the present invention flaw gates are used to process and record ultrasonic reflector indications detected during a scan. The flaw gates each record key task parameters such as scanner position or surface time directly in the flaw gate so that the parameter can be immediately recorded along with wave amplitude and transit time information, and used to correct transit time information. The flaw gates in the preferred embodiment select and record, as a reflection indication, only the largest amplitude signal, as compared to a threshold, within a time window which can correspond to depth or location within the material being inspected; however, it is possible for the flaw gate to record up to 256 indications in each window. The starting and stopping of data acquisition and threshold comparsion can be independently triggered to control the accuracy of the placement and resolution of each window. The transit time offset available in the flaw gate can be used to correct for misalignment of the transducer, geometry variations of the surface being inspected, changing immersion fluid or inspected material temperature or any other condition that requires a change in the reference time at which amplitude threshold comparisons are started.

The flaw gates are arranged in pairs so that data is processed and recorded in one flaw gate while the other flaw gate in the pair can transfer flaw indications and corresponding transducer positions to a main computer. The alternating of the flaw gates during data collection and processing insures that data is not lost when a large number of reflector indications are detected in the window of a particular flaw gate pair. It is also possible to alternate the use of the flaw gates in a pair in synchronization with other parameters such as time, position or scan direction. The use of multiple pairs of flaw gates allows the burden of processing on each flaw gate pair to be reduced by dividing flaw gate data acquisition into windows according to transducer, position or material depth. In the preferred embodiment, the two flaw gates in each pair are assigned to different scan directions in the inspection system. That is, the preferred scan method alternates between clockwise and counterclockwise full 360° rotations of the scan head with an axial index in a rotor bore at each rotation reversal. One flaw gate in the pair samples and processes data during the clockwise rotation and the other during the counterclockwise rotation. The circumferential position of the transducer is provided to each flaw gate during each scan. In the preferred embodiment there are six pairs of flaw gates plus a thirteenth special purpose flaw gate for each scanning transducer. Each pair of flaw gates is dedicated to a specific range of material depth or a time window. Each active flaw gate also performs corrections on time of flight data to compensate for eccentricity and wobble of the scan head relative to the rotor bore to insure that reflector positions are properly recorded. The thirteenth flaw gate is used to collect the ranging data, which corresponds to a time of flight and transducer position, used for this correction.

A control computer 10 initiates an inspection through an interface driver 12 by signalling axis control computers 14 over a main CPU bus 16. The axis control computers 14 control axis control motors 18 mechanically linked to one or more array transducers 20 and physically coupled to a ranging transducer 22 to move the scan head to the desired positions. The apparatus for moving the scan head is discussed in detail in the related application entitled BORESONIC INSPECTION SYSTEM. A resolver 24 sends transducer position information back to the axis control computers 14 which transfers it to the flaw gates over bus 30. After the transducer 20 is in position, a timing control unit 26 initiates a pulse control unit 28 over the control and data bus 30. The data bus 30 is a multipurpose bus that is 60 bits wide with groups of bits dedicated to tasks such as control signals and digitized data transfer. The pulse control unit 28 initiates a pulse transmisssion by either the array transducer 20 or ranging transducer 22. The return signals from the transducers 20 and 22 are multiplexed according to the transducer activated, and are attenuated according to the depth of a return signal window in the material being inspected by analog multiplexer 32. The analog multiplexer also rectifies the return signal before application to digitizer 34 over bus 30. The digitizer 34 continuously digitizes the transducer signal and applies the digitized return signal to flaw gate 36-42.

The flaw gates 36-42 operate in channel pairs where each channel is active over a time window corresponding to the depth in the inspected material at which a reflection can occur. The timing control unit 26 controls the opening of the window for each channel while the digitizer 34 transmits load or write control pulses to all of the flaw gates 36-42 whenever a sample is digitized. Each flaw gate stores the digitized transducer return signal values in a waveform memory for its corresponding window. Each flaw gate then shifts a threshold waveform by a transit time offset that is a function of rotation position and that indicates changes in relative position of the array transducer 20 and the material being inspected. Subsequently, each flaw gate compares the stored return signal waveform with the shifted threshold waveform and stores the peak amplitude, start time, peak time and stop time of each signal excursion above the threshold curve. These signal excursions are reflector indications which can indicate 5 flaws. The axis control computers 14 indicate the position of the transducer 20 to the flaw gates 36-42 for each scan, and the transducer position along with the reflector indication data is transferred over the main computer bus 16 and through the interface driver 12 to control computer 10. The control computer 10 then determines the locations of flaws based on the known geometry of the ultrasonic beam path in the immersion fluid and the material being inspected.

The flaw gates 36-42 are arranged in pairs so that during a clockwise scan, one of the flaw gates collects and processes data while during a counterclockwise scan the other of the flaw gates collects and processes data. During the period in which a gate is not collecting and processing transducer data the gate is available for transferring reflection indication data to the control computer 10. In FIG. 1, the flaw gates, etc. are shown for a single transducer for simplicity of explanation; however, in practice, several inspection transducers are used for an inspection and, as a result, the circuits 26-42 would be duplicated for each inspection transducer in an actual system. It is also possible to assign one pair of flaw gates to a number of fixed focus transducers or to a single variable focus transducer having several different focal depths.

The timing control unit 26 generates the data and control bus signals shown in FIG. 2B. The sync pulse 44-1 controls generation of the ultrasonic wave at the transducer. The delay sync pulse 44-2 occurs at the start of a data window that is delayed from the beginning of the sync pulse by the time segment 44-5. The data window signal 44-3 determines the width of the digitized data that is loaded into one of the flaw gates 36-42. Channel code lines (ch0-ch5) 44-4 uniquely identify a channel for the purposes of controlling the loading of data into a particular flaw gate, the transmit routing of the sync pulse, the amplifier input channel and the amplifier input attenuation.

A timing cycle is the period between sync pulses and is decomposed into 4 separate segments. Time segment #1 44-5 is from the sync pulse to the delay sync pulse. Time segment #2 44-6 goes from the delay sync pulse to the end of the data window. Time segment #3 44-7 goes from the end of the data window to an arbitrary point that is typically several hundred microseconds before the next sync pulse. Time segment #4 goes from the end of time segment #3 to the next sync pulse. The channel lines 44-4 are changed at the end of time segment #3 44-7. The purpose of time segment #4 is to allow electronics, which are multiplexed on the line by the changing channel lines, to settle before the next sync pulse is generated.

Figure 2A:
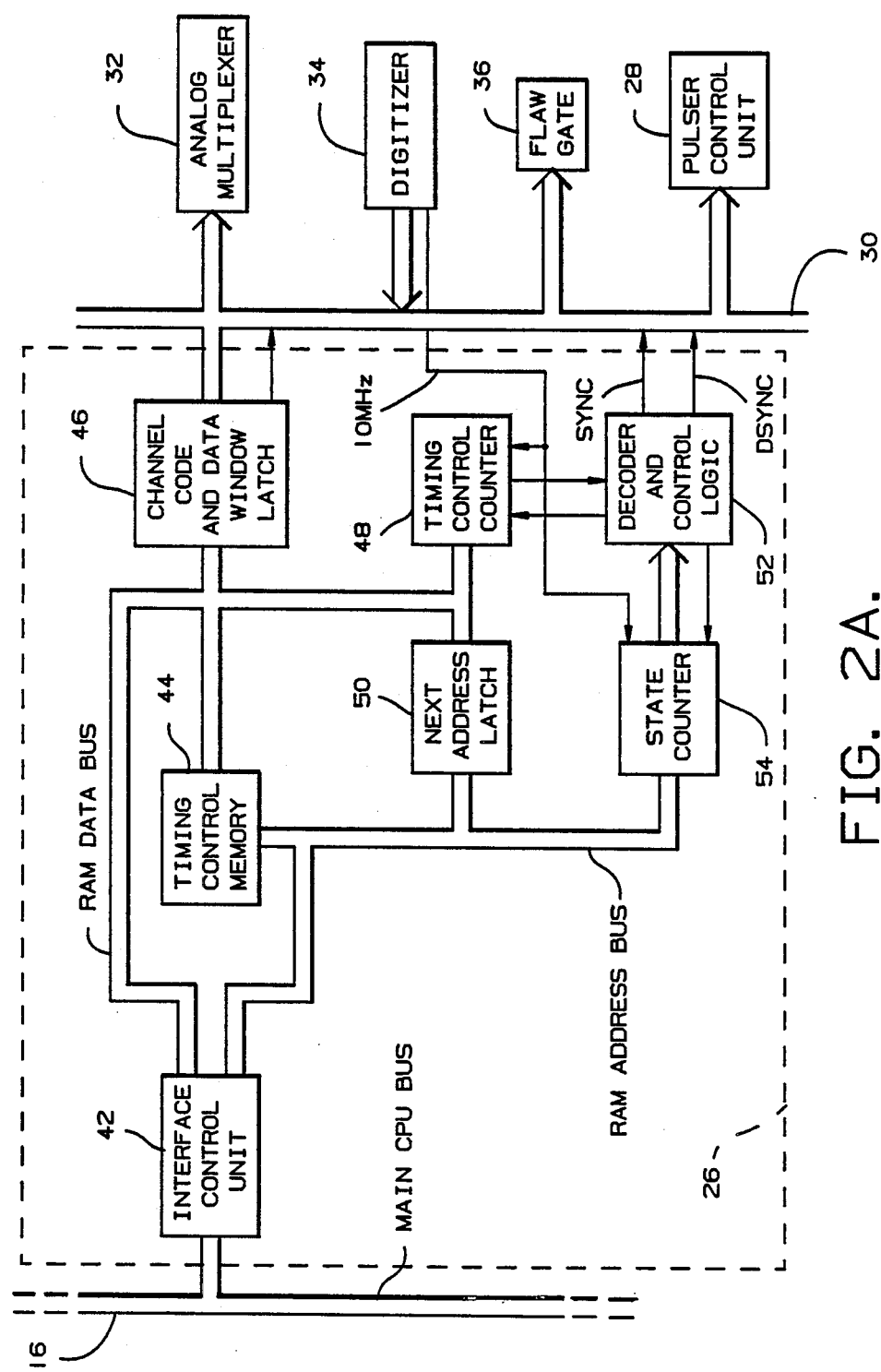
FIG. 2A illustrates the details of the timing control unit 26 of FIG. 1.

The timing control unit 26 is controlled by the timing control memory 44 of FIG. 2A which is a random access memory (RAM) that is loaded by the control computer 10 through the main bus 16 and via an interface control unit 42. The timing control memory 44 contains data for controlling each of the 4 time segments shown in FIG. 2B. Each of the time segments is defined by 8 8-bit words in the timing control memory 44 as shown in the segment memory map table below:

| WORD | DESCRIPTION |
|---|---|
| 0 | Reserved - Not Used |
| 1 | Timing Counter Low Byte |
| 2 | Timing Counter Middle Byte |
| 3 | Timing Counter High Byte |
| 4 | Channel Code and Data Window Bits |
| 5 | Pulse Control Bits |
| 6 | Next Address |
| 7 | Reserved - Not Used | of the 8 words, word 0 is reserved and not used. Word 1 contains the preset value for the timing counter low byte (bits 0-7). Word 2 contains the timing counter preset value for the middle byte (bits 8-15). Word 3 contains the counter preset value for the high byte (bits 16-23). Word 4 contains the channel code bits and the data window bit as shown in the channel code and data window bit map table below:

| Channel Code and Data Window Bit Map Table | | |
|---|---|---|
| BIT | NAME | DESCRIPTION |
| 0 | CH0 | Channel Code Bit 0 |
| 1 | CH1 | Channel Code Bit 1 |
| 2 | CH2 | Channel Code Bit 2 |
| 3 | CH3 | Channel Code Bit 3 |
| 4 | CH4 | Channel Code Bit 4 |
| 5 | CH5 | Channel Code Bit 5 |
| 6 | WIN | Data Window Bit |
| 7 | — | Not Used |

Bits 0-5 control ch0-ch5, the channel code lines, and bit 6 controls the data window. When bit 6 is logic state 1, the data window is active on the data and control bus 30 during the entire segment. Word 5 controls the sync and delay sync pulse generation as shown in the pulse control bit map table below:

| Pulse Control Bit Map Table | |
|---|---|
| BIT | DESCRIPTION |
| 0 | Sync Control Bit |
| 1 | Delay Sync Control Bit |
| 2-7 | Not Used |

Bit 0 of word 5 causes a sync pulse to be generated when it is a logic state 1. Bit 1 of word 5 causes a delay sync pulse to be generated when it is a logic state 1. Word 6 is the 8 higher order address bits of the timing control memory 44 for the next segment to be executed. Word 7 is reserved and is not used.

Figure 2C:
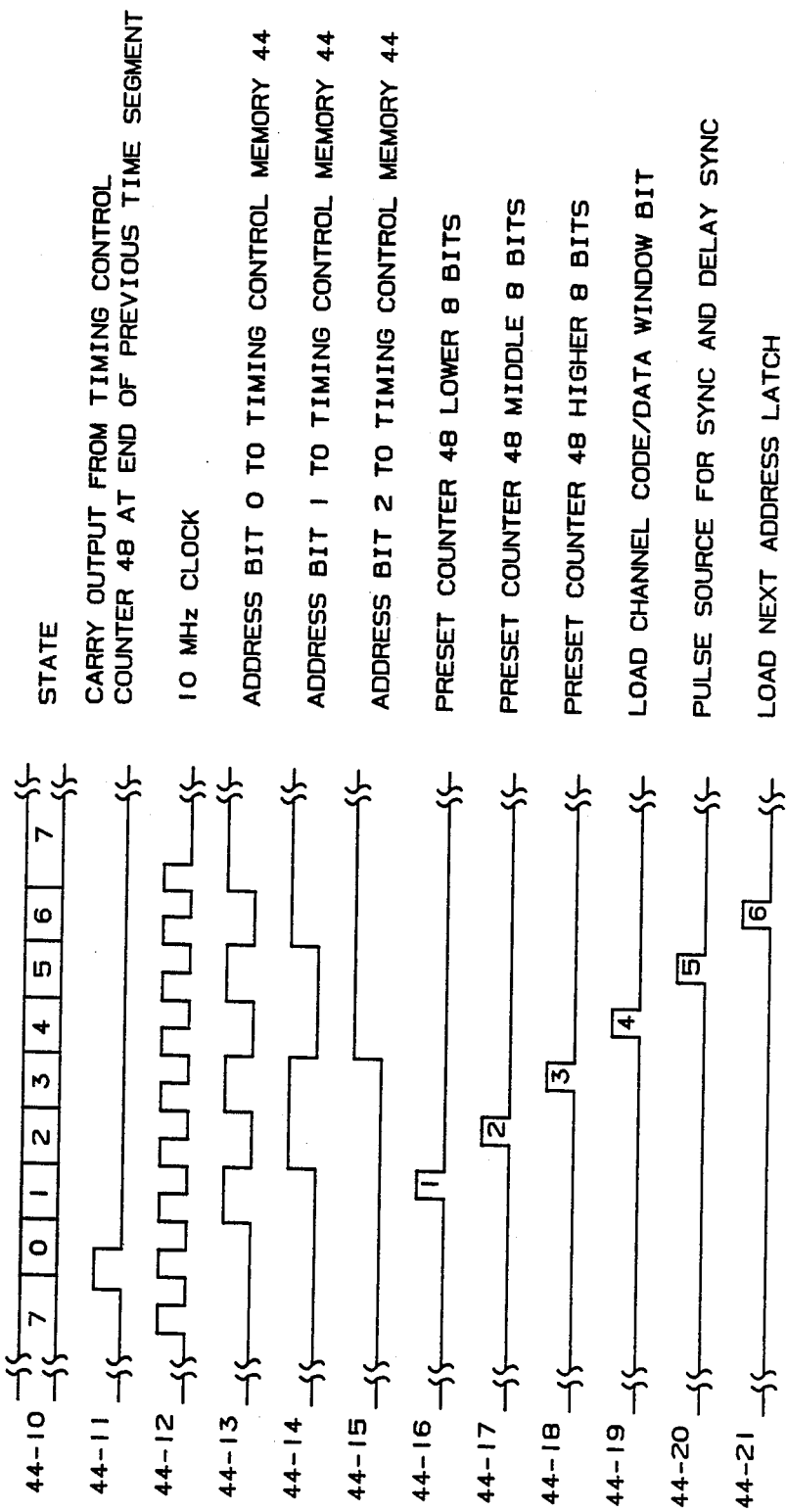

A normal, complete timing cycle consists of consecutive execution of four properly configured segments by the timing control unit 26. Referring to FIG. 2C, at the end of segment #4 of the previous sync interval, a carry signal 44-11 out of the timing control counter 48 occurs when the timing control counter counts down to zero. This carry signal is input to decoder and control logic 52, which resets state counter 54 as shown in 44-10 of FIG. 2C from a state 7 to a state 0. The state counter 54 then sequences through states 0 to 6 and holds at the 7th state. The clocking from one state to the next is synchronous with the 10 MHz clock 44-12. The state counter output lines 44-13, 44-14 and 44-15 are the lower 3 address bits of the timing control memory 44. As the state counter 54 counts from 0 back up to 7, the different states are decoded by decoder and control logic 52.

The 1 state 44-16 presets the lower 8 bits of the timing and control counter 48. The 2 state 44-17 presets the middle 8 bits of counter 48. The 3 state 44-18 presets the upper 8 bits of counter 48. The 4 state 44-19 loads the channel code and data window bit into the channel code and data window latch 46. The 5 state 44-20 generates the sync and delay sync pulses on the data and control bus 30. The 6 state 44-21 loads the next address latch value which sets the higher 8 address bits of the timing control memory 44. After the state counter 54 has reached state 7, the timing control counter 48 is enabled and begins to count to zero. The amount of time that it takes to count to zero is determined by the counter preset values that were loaded from locations 1, 2 and 3 of timing control memory 44 during states 1, 2 and 3 of the state counter 54.

For the first segment of a timing cycle, the state counter first sequences through states 1, 2 and 3 to load the counter 48 with the segment #1 timing values. During state 4, the channel code and data window bits are latched. For segment #1, the data window bit is a logic state 0. During state 5, the decoder and control logic 52 generates a sync pulse by ANDing pulse source signal 44-20 with the sync control bit 44-48, which is a logic state 1 (bit 0 of RAM location 5 44-35). The delayed sync pulse is not generated because the delay sync control bit 44-49 is a logic state 0 (bit 1 of RAM location 5 44-48). During state 6, the next address latch 50 is loaded. After state 7 is reached, the timing control counter then counts down to zero. When it reaches zero, the carry output pulse 44-11 is sent to the decoder and control logic 52 which in turn triggers state counter 54 to initiate another cycle beginning at the RAM address set by the next address latch 50. For proper operation, the next address word from segment #1 must correctly point to the area in the timing control memory 44 that contains the data for segment 2.

For the second segment, the state counter again sequences through states 1, 2 and 3 to load the counter 48 with the segment #2 timing values. During state 4, the channel code and data window bits are latched. For segment #2, the channel code is the same as for segment #1 but the data window bit is a logic state 1 which causes the data window to be high on the control and data bus 30 throughout segment #2. During state 5, the decoder and control logic 52 generates a delay sync pulse by ANDing pulse source signal 44-20 with the dalay sync control bit 44-49, which is a logic state 1. The sync pulse is not generated because the sync control bit 44-48 is a logic state 0. During state 6, the next address latch 50 is loaded. After state 7 is reached, the timing control counter 48 then counts down to zero, which triggers the initiation of another cycle beginning at the RAM address for segment #3 set by the next address latch 50.

During the third segment state 1-3, the counter 48 is loaded with the segment #3 timing values. During state 4, the channel code and data window bits are latched. For segment 3, the channel code is the same as for segments 1 and 2, however, the data window bit is a logic state 0 which causes the data window to be low on the control and data bus 30. During state 5, neither a sync pulse nor a delay sync pulse are generated because the sync and delay sync control bits 44-48 and 44-49 are both logic state 0. During state 6, the next address latch 50 is loaded. After state 7 is reached, the timing control counter 48 then counts down to zero, which triggers the initiation of another cycle beginning at the RAM address for segment #4 set by the next address latch 50.

During states 1-3 of the fourth segment, the counter 48 is loaded with the segment #4 timing values. During state 4, the channel code and data window bits are latched. For segment #4, the channel code changes to the code for the next timing cycle. The data window bit is a logic state 0 which causes the data window to be low on the control and data bus 30. During state 5, neither a sync pulse nor a delay sync pulse are generated because the sync and delay sync control bits 44-48 and 44-49 are both logic state 0. During state 6, the next address latch 50 is loaded. After state 7 is reached, the timing control counter 48 then counts down to zero, which triggers the initiation of another cycle beginning at the RAM address set by the next address latch 50. For proper operation, the next address word from segment #4 must correctly point to the area in the timing control memory 44 that contains the data for segment #1 of the next timing cycle.

In the preferred implementation, there are a maximum of 32 channels (windows) with 4 timing segments for each channel. To pulse all 32 channels, the next address word for a segment must point to the proper data area for the next segment and channel. To pulse just one channel repetitively, the next address word for segment 3 must point to the beginning of the segment #4 where the channel code is set. Then, if the timing control unit 26 is started at the beginning of segment 4, it would cycle through segments 1, 2, 3 and 4 for the selected channel.

Figure 3:
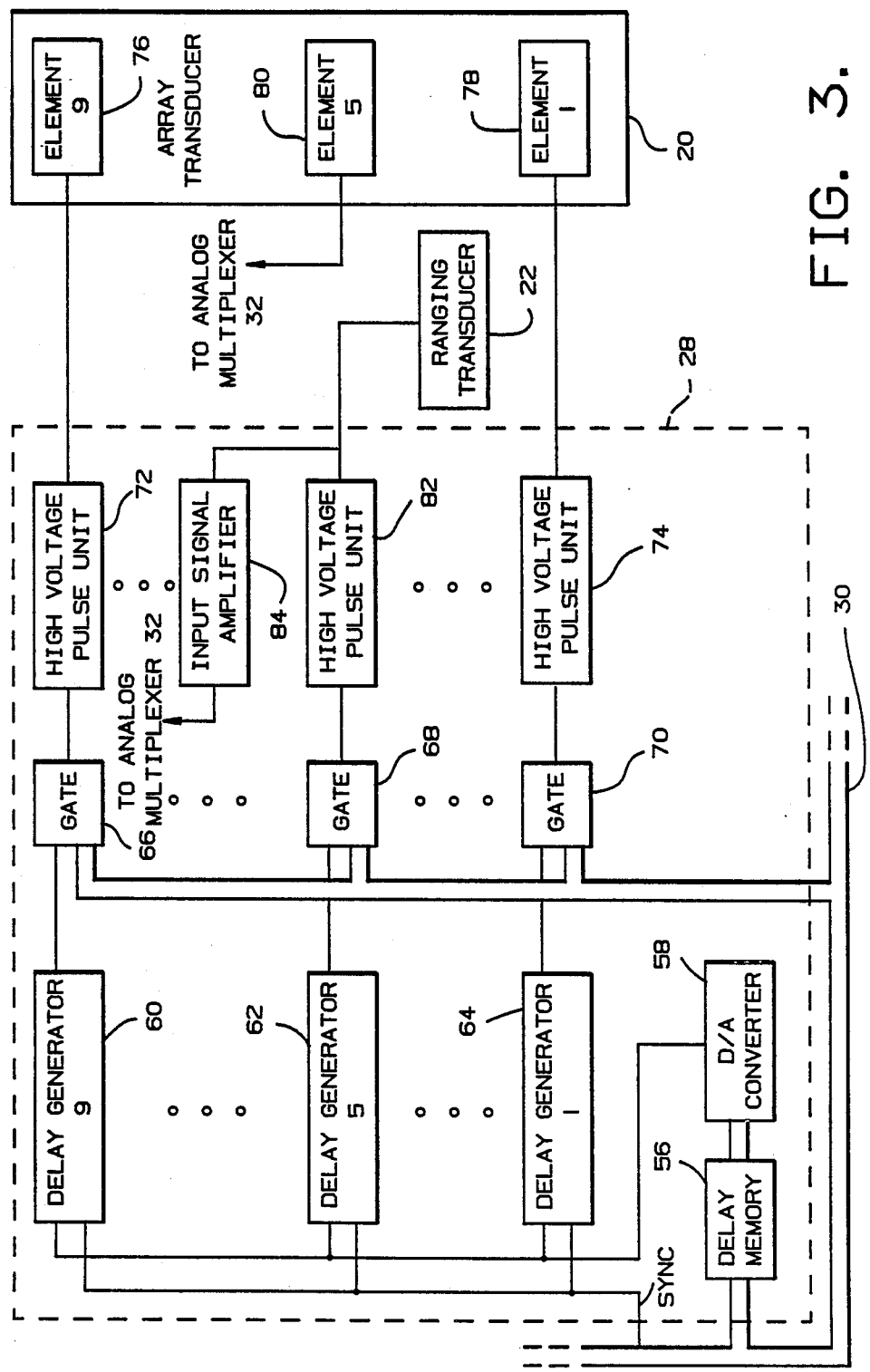
FIG. 3 depicts the details of the pulse control unit 28 of FIG. 1.

The channel control code is applied to a delay memory of RAM 56 in the pulse control unit 28 as illustrated in FIG. 3. The channel control code acts as an address for outputting a delay word applied to a digital-to-analog converter 58. The memory 56 can be loaded by the control computer 10 over bus 16 with appropriate delay words for different depths although this connection is not shown in FIG. 3. The digital-to-analog converter 58 produces an analog voltage of from zero to nine volts which controls the beam focus of the array transducer 20 through eight programmable delay generators 60-64. A preferred nine element array transducer is available from the New York Institute of Technology and will produce a focussed beam one millimeter in diameter at the focal point. The delay generators 60-64 each include appropriate delay circuits to produce suitable delays for focussing within the material to be inspected. The implementation of the delay can be performed by using voltage variable capacitors in standard one-shot circuits. When pulses to each transducer element are delayed by appropriate values as a function of voltage output by the digital-to-analog converter 58, the focal point moves from near the surface to deeper within the material as the voltage changes from nine to one volts. Typical delay values for each element as a function of voltage are shown in the transducer delay table below for the preferred nine element transducer:

| Transmit Voltage | \multicolumn{8}{c}{TRANSDUCER DELAY TABLE — TRANSDUCER ELEMENT} |
|---|---|---|---|---|---|---|---|---|

| Transmit Voltage | 1 | 2 | 3 | 4 | 6 | 7 | 8 | 9 |
|---|---|---|---|---|---|---|---|---|
| | \multicolumn{8}{c}{Time Delay (microseconds)} |
| 1 | 0.00 | 0.14 | 0.28 | 0.42 | 0.70 | 0.85 | 0.99 | 1.14 |
| 2 | 0.00 | 0.11 | 0.22 | 0.33 | 0.56 | 0.65 | 0.77 | 0.88 |
| 3 | 0.00 | 0.08 | 0.15 | 0.22 | 0.37 | 0.44 | 0.53 | 0.60 |
| 4 | 0.00 | 0.04 | 0.08 | 0.11 | 0.18 | 0.22 | 0.26 | 0.30 |
| 5 | 0.00 | 0.00 | 0.00 | 0.00 | 0.00 | 0.00 | 0.00 | 0.00 |
| 6 | 0.00 | −0.04 | −0.06 | −0.09 | −0.16 | −0.19 | −0.22 | −0.27 |
| 7 | 0.00 | −0.06 | −0.11 | −0.17 | −0.30 | −0.36 | −0.42 | −0.49 |
| 8 | 0.00 | −0.07 | −0.16 | −0.23 | −0.42 | −0.52 | −0.60 | −0.69 |
| 9 | 0.00 | −0.09 | −0.19 | −0.30 | −0.53 | −0.65 | −0.76 | −0.87 |

Element 5 does not have delay values for reasons that will become apparent later. An analog voltage of nine volts will cause the beam to focus near the surface in the material, a voltage of five volts will cause focus to be at the focus value determined solely by the lense of transducer 20 (the geometric focal point), while a one volt analog signal will focus the transducer at maximum depth in the material beyond the geometric focal point. The geometric focal point is the focal point obtained when all of the elements fire in phase, which is the five volt case in the above table. It is sometimes desirable to pulse various combinations of transducer elements. The circuit of FIG. 3 has the ability to control which elements are pulsed through the action of gates 66–70. A sync signal from data and control bus 30 is transferred through each delay generator with the specified delay. Selection gates or switches 66–70 are controlled by a pulse code from the analog multiplexer 32 transferred over the data and control bus. The specific codes used, or rather elements to be pulsed, depends on the details of the particular ultrasonic inspection. However, the usual case is to pulse all elements but element five.

The output of the gates corresponding to programmable delay generators 1–4 and 6–9 are transferred through high voltages pulse units 72–74 to appropriate elements 76–78 in the array transducer 20. The middle or fifth element 80 of the array transducer 20 is used as the return signal receiver transducer and is connected to the analog multiplexer 32 as will be discussed later. The fifth delay generator 62 through its gate 68 and high voltage pulse unit 82 activates the ranging transducer 22. The return signal from the ranging transducer 22, which indicates the surface of the material being inspected is amplified by input signal amplifier 84 and then applied to the analog mulitplexer 32.

Figure 4:
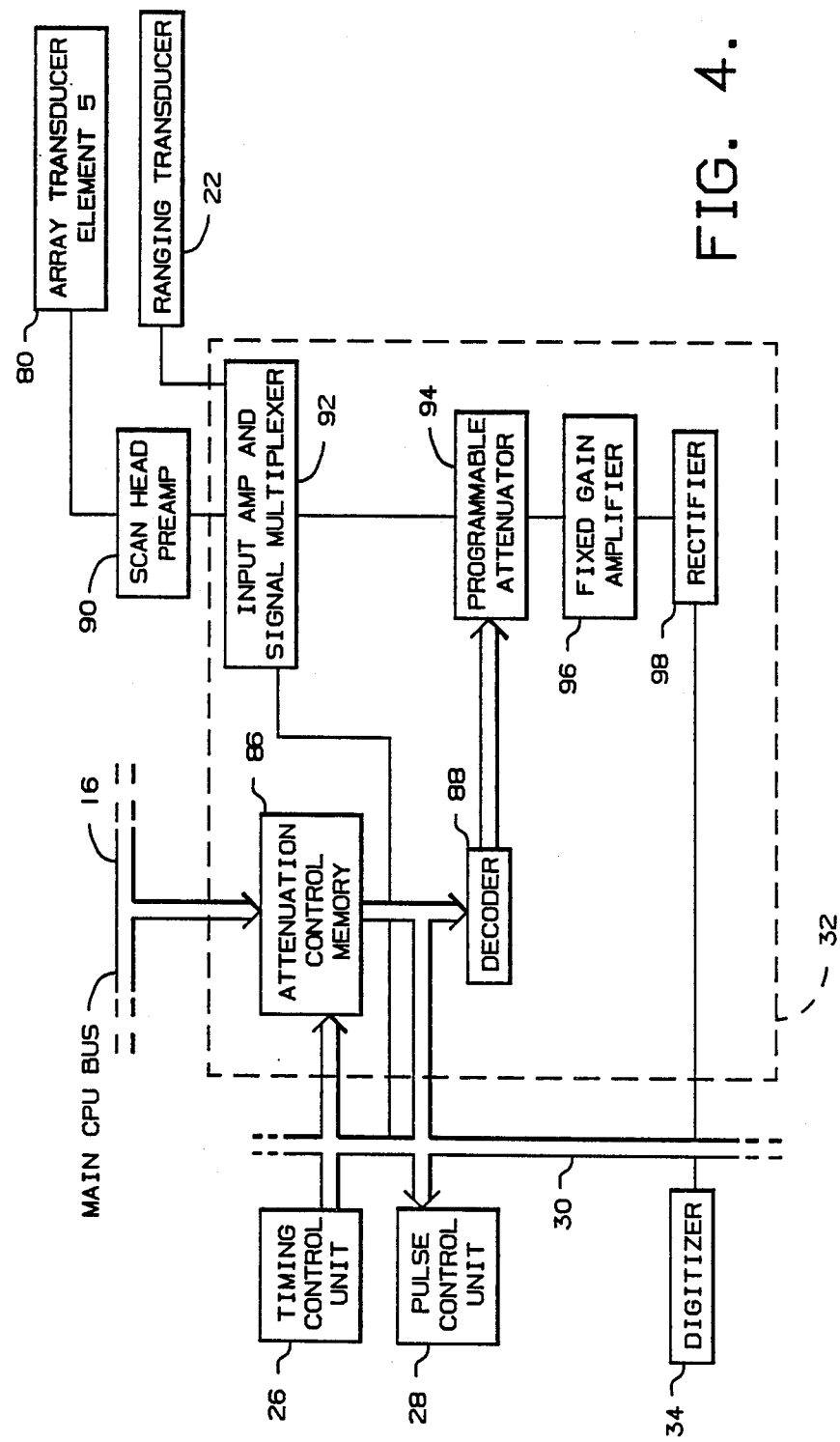
FIG. 4 illustrates the components of the analog input multiplexer 32 of FIG. 1.
Figure 5:
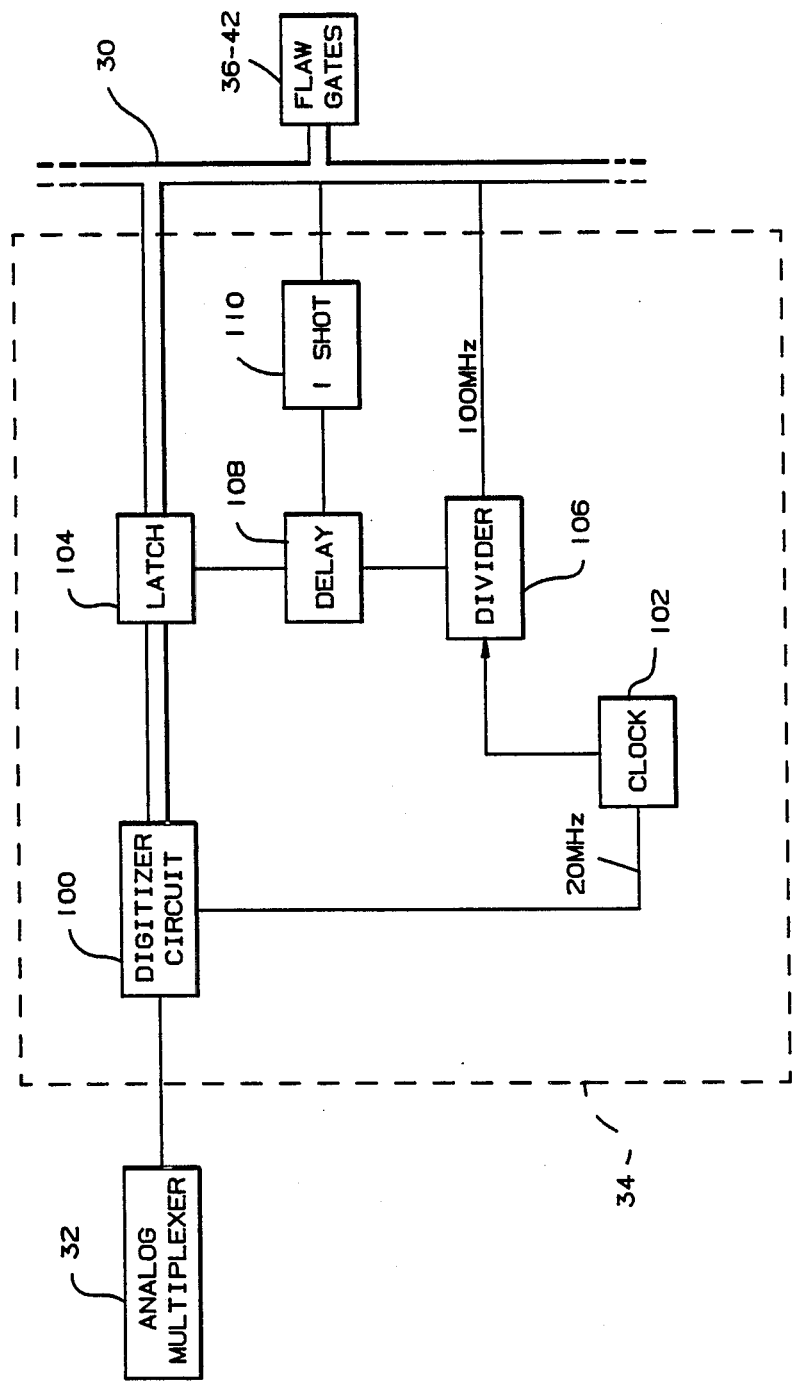
FIG. 5 depicts the details of the digitizer 34 of FIG. 1.

The analog multiplexer 32 of FIG. 4 receives the channel code from the timing control unit 26 over control bus 30. The channel code is applied to an attenuation conrol memory 86 which produces an attenuation contorl word, part of which is applied to decoder 88. The attenuation control word also includes a pulse control word which is applied to the pulse control unit 28, as previously discussed, to control which transducer elements in array transducer 20 receive a high voltage pulse and a receive control bit which is applied to the input amplifier and signal multiplexer 92. The attenuation control memory 86 is loaded by control computer 10 over bus 16. The return inspection echo received by array transducer element five 80 is amplified by a scan head preamplifier 90 producing a differential signal applied to an input amplifier and signal multiplexer unit 92. The analog multiplexer portion of unit 92 selects either the signal from array transducer element five 80 or from the ranging transducer 22 based upon the receive control bit. The amplifier portion of unit 92 includes is a differential amplifier that reduces line noise. The selected signal is applied to a programmable attenuator 94 which is controlled by decoder 88 based on the attenuation control word produced by attenuation control memory 86. The programmable attenuator 94 selects an attenuation path therethrough based on the decoder 88 output using analog gates where the paths are stepped in 4 dB increments for eight steps. The attenuation is required when the inspection system is looking for flaws near the surface of the material being inspected and decreases in magnitude with depth. The attenuation necessary is determined by experimentation during calibration and it is the amount necessary to bring return signals from a reference reflection into a specified range which is typically 0.4 volts as measured at the digitizer 34 input. The attenuated signal is applied to a fixed gain amplifier 96 and then to a half-wave rectifier 98. The half wave rectifier 98, consistent with standard ultrasonic signal processing techniques, converts the sinusoidal return signal into a rectified signal that includes only positive values. The rectified signal is then applied to digitizer 34 over bus 30. For analysis of more subtle features of the echo return signals, the return signals can be directly passed around the rectifier without rectification via a control signal over bus 16 although this connection is not shown in FIG. 4. The rectified signal is continuously digitized by a digitizer circuit 100 (FIG. 5) obtainable from TRW which digitizes 20 million samples a second based on a 20 MHz clock signal produced by clock 102. The clock 102 controls a sample latch 104 through a divider 106 and delay unit 108. When the latch 104 has stabilized it applies the digitized value to the flaw gates 36–42 over the control and data bus 30. The flaw gates 36–42 are activated to load the latest sample value by one shot 110 which produces a write pulse.

Figure 6:
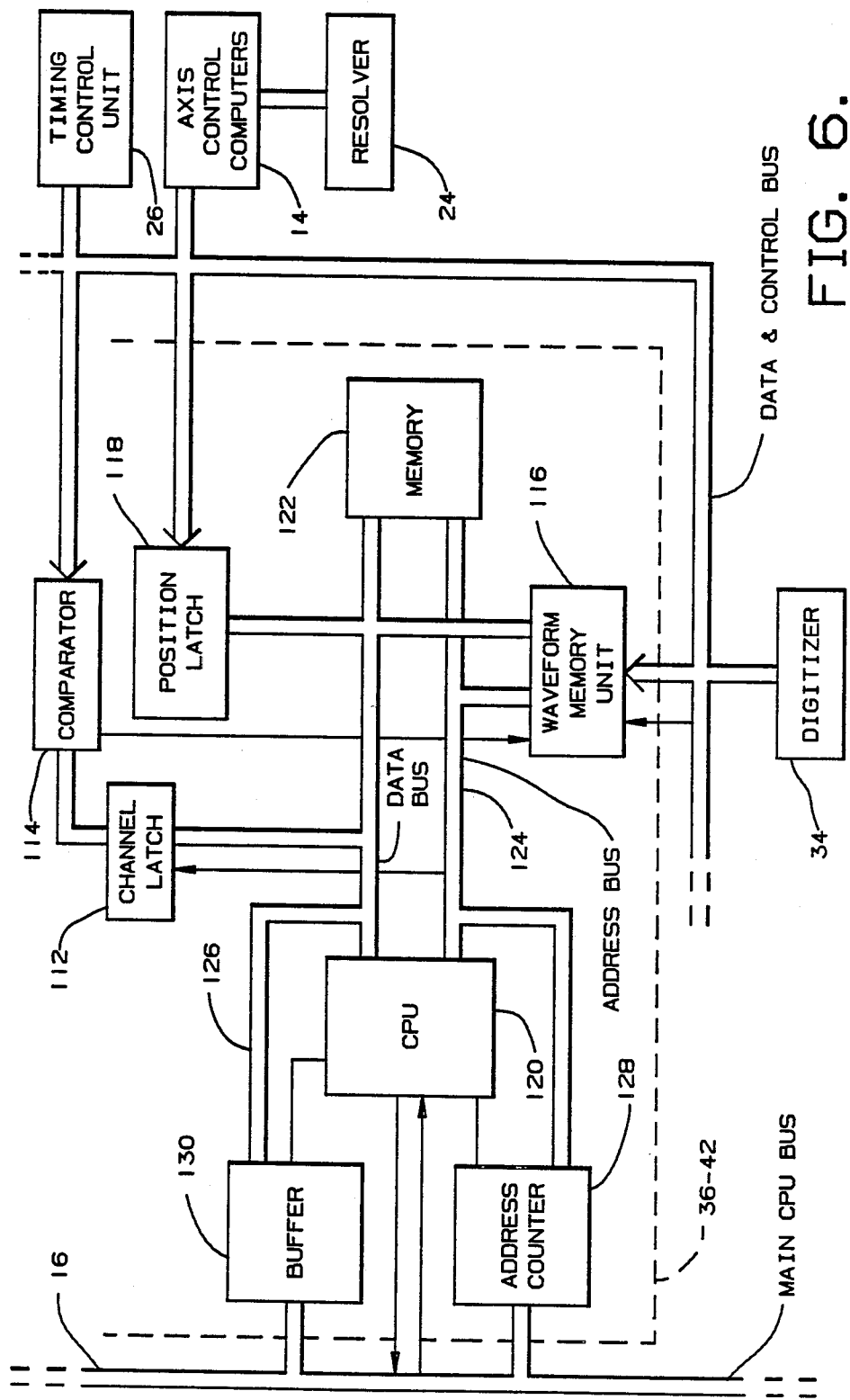
FIG. 6 illustrates the components of the flaw gates 36-42 of FIG. 1.

When the timing control unit 26 outputs a data window signal 44-3 and simultaneously outputs a channel code that matches the channel code produced by the channel latch 112 in the flaw gate of FIG. 6, a comparator 114 produces a write enable signal that activates waveform memory unit 116 to accept the latest digitized sample from digitizer 34 in synchronization with the write signal produced by the digitizer 34. The waveform memory unit 116 continues to store the digitized samples as long as the data window signal 44-3 is a locic 1 state and the channel code produced by the timing control unit 26 selects this particular flaw gate. That is, the waveform memory 116 unit is active for storing a return signal waveform during the data window associated with the particular flaw gate as designated by the channel code. CPU 120 is preferably a Z80 microprocessor available from Zilog and is capable of analyzing a 10 microsecond waveform sampled at about 0.05 microseconds in about 20 milliseconds with a threshold curve that is also 10 microseconds wide with amplitude values specified in steps of 0.1 microseconds. The window during which data samples are stored is adjustable in 0.1 microsecond steps. If higher processing speed is required, an appropriate higher speed processor should be substituted for the Z80 microprocessor.

At some time during the open window, preferably at the beginning or end, the position signal produced by resolver 24 is transferred from position latch 118 by CPU 120 into memory 122. The memory 122 includes a programmable read only memory portion which contains the control routine for CPU 120. The memory 122 also includes RAM variable areas for storing values such as the channel code to be stored in channel latch 112 and the position from position latch 118. Memory 122 also stores a ranging curve of transit time offset values produced by the ranging transducer from samples taken at various positions on the material surface. The value of the ranging curve at each inspection position is used to adjust the start point for a comparison between a threshold curve, also stored in memory 122 and the return signal waveform stored in the waveform memory unit 122. The return signal waveform stored in the waveform memory 116 is compared by the CPU 120 to the threshold in waveform in memory 122 one sample at a time where one threshold point is used for every two signal waveform points. The rising crossing time, the peak time, the amplitude at the peak time and the falling crossing time of excursions of the return signal waveform above the threshold waveform are stored in memory 122 as reflector indications. A detailed description of the threshold comparision operation performed by CPU 120 as well as the flaw location determination by control computer 10 will be discussed in more detail later.

Once a complete scan is finished or when the indications portion of memory 122 is full, CPU 120 will release control of the flaw gate address bus 124 and the data bus 126 when a bus request signal is received from the control computer over bus 16. When buses 124 and 126 have been released CPU 120 responds to the control computer 10 with a bus release acknowledge signal. The control computer 10 then addresses memory 122 through address counter 128 and reads out the position and indication data through buffer 130. The control computer 10 then processes the reflection indication and position data to determine flaw locations.

Figure 7:
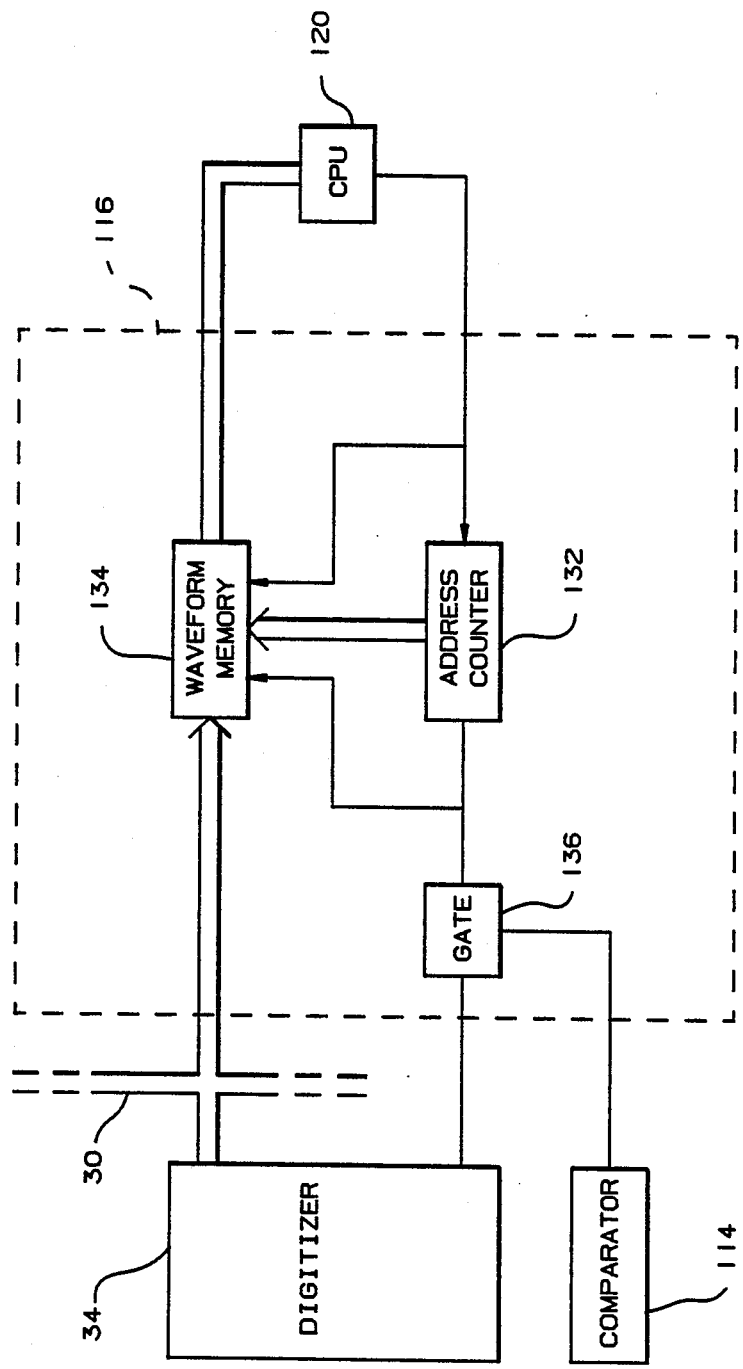
FIG. 7 illustrates the waveform memory unit 116 of FIG. 5.

FIG. 7 illustrates the components of waveform memory unit 116. At the beginning of each scan cycle CPU 120 resets address counter 132 to the first location in waveform memory 134 and enables memory 134 to accept data. When the digitizer 34 has placed a sample value on the data and control bus 30 it sends a write or load signal to waveform memory 134 which then stores the latest digitized value therein. If the flaw gate has its window open, comparator 114 produces a write enable signal which opens gate 136. When the write signal is received by the waveform memory 134 through gate 136, the waveform memory 134 stores the digitized return signal sample at the address designated by the address counter 132. The write pulse is delayed by address counter 132 and then used to increment the storage location address for the waveform memory 134 in anticipation of the next digitized return signal sample. When the window for a particular flaw gate has expired the CPU 120 changes waveform memory 134 from an input mode to an output mode, and resets address counter 132 to the beginning of the memory 134. CPU 120 then increments address counter 132 to read out the return signal waveform and make the threshold comparison, as discussed below. The memory 134 should hold at least fifty microseconds of scan data so that low resolution high speed scans are possible when desired and be capable of loading at a 20 MHz rate.

Figure 8:
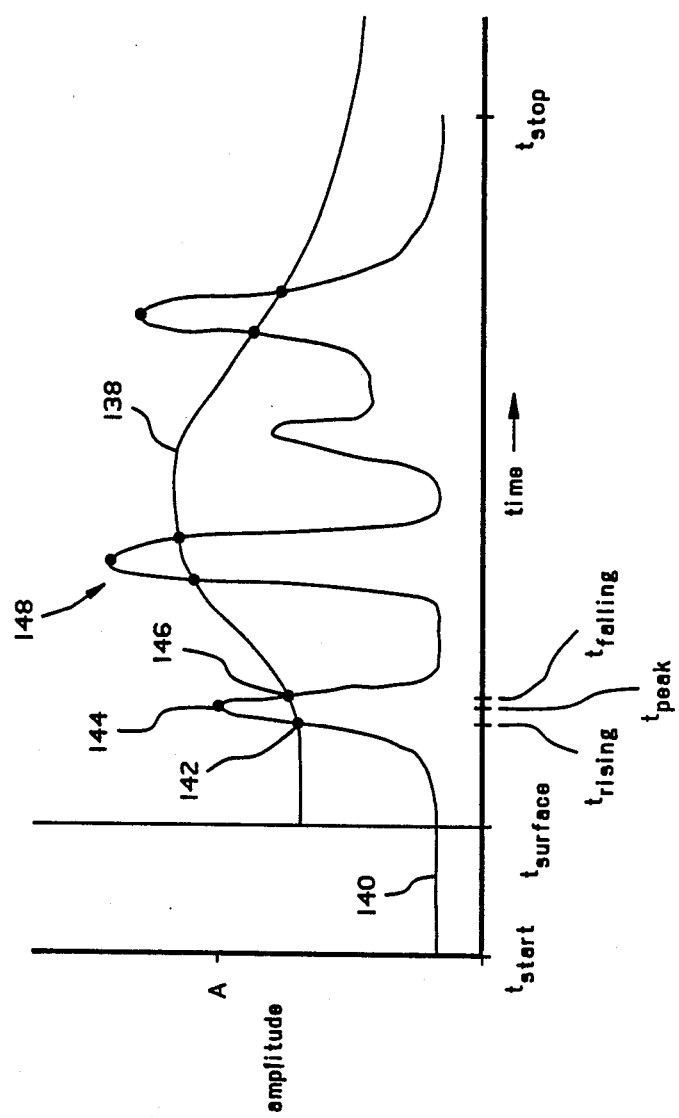
FIG. 8 shows a threshold curve used to obtain reflector indications from a return ultrasonic signal.

FIG. 8 illustrates the threshold comparison process using continuous curves which represent the discrete one microsecond sample points of both the threshold curve 138 and the 0.05 microsecond sample points of the signal waveform 140. The threshold curve 138 is shifted from the start $t_{start}$ of the flaw gate sample window by a surface time $t_{surface}$. The surface time is obtained from the ranging curve produced by the ranging transducer 22. This shifting can be accomplished by reading out the data samples from waveform memory 134 and discarding samples until the offset adjustment has been accomplished. Once the surface time offset has been performed each of the return signal data samples is compared to the appropriate corresponding threshold value with one threshold point used for every two signal data samples. When the return waveform value first equals or exceeds the corresponding threshold value at, for example, point 142, the rising crossing time $t_{rising}$ is stored. The crossing time is computed from the difference between the addresses of the rising crossing time sample and the surface time sample, where each memory location corresponds to 0.05 microseconds. When the peak of the excursion is reached at, for example, point 144, both the amplitude A and the time of the peak $t_{peak}$ are stored. In addition, when the waveform excursion above the threshold crosses back below the threshold curve 136 the falling crossing time at, for example, point 146, is stored. The times $t_{rising}$, $t_{peak}$ and $t_{falling}$ along with the absolute amplitude A of the excursion at the peak time comprise a reflection indication. It is possible to store all the indications which occur during a window, however, in the preferred embodiment only the maximum amplitude excursion indication 148 and up to 10 additional excursion indications are stored as determined by the operator. As can be seen from FIG. 8 some of the peaks in the return echo signal do not cross the threshold and therefore are not stored as indications.

The threshold curve 138 is obtained by bouncing ultrasonic pulses off of known depth (time of flight) and known minimum size reflectors in a calibration block, and recording the maximum amplitude of the signals returned for each known depth reflector. The maximum amplitude signals plotted with respect to time produce the threshold curve, that is, the threshold curve is a distance versus amplitude correction curve for a particular depth/time window.

Figure 9A:
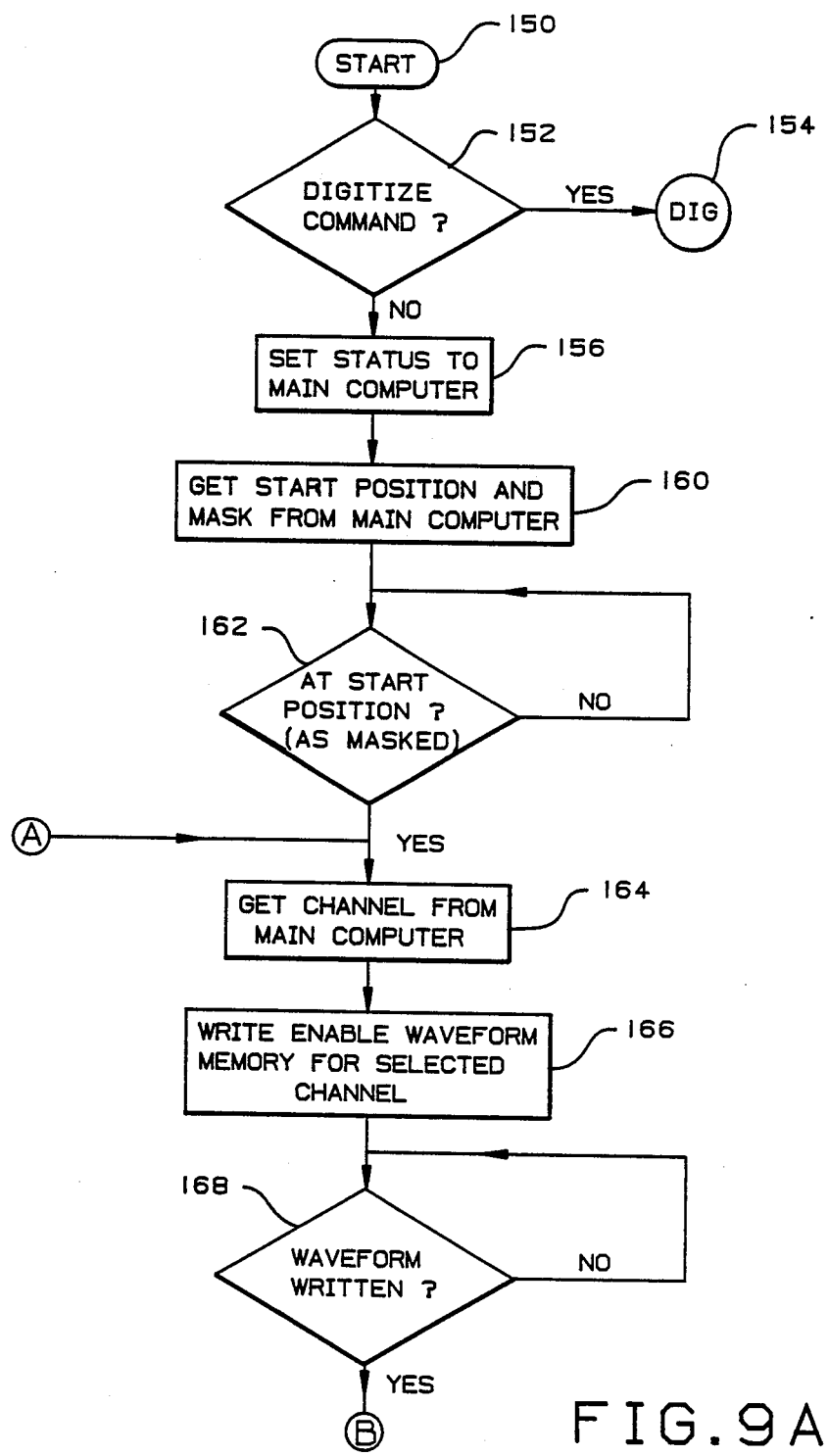
FIGS. 9A-9B and 9C depict the procedure performed by the CPU 120 in the flaw gate depicted in FIG. 6.
Figure 9B:
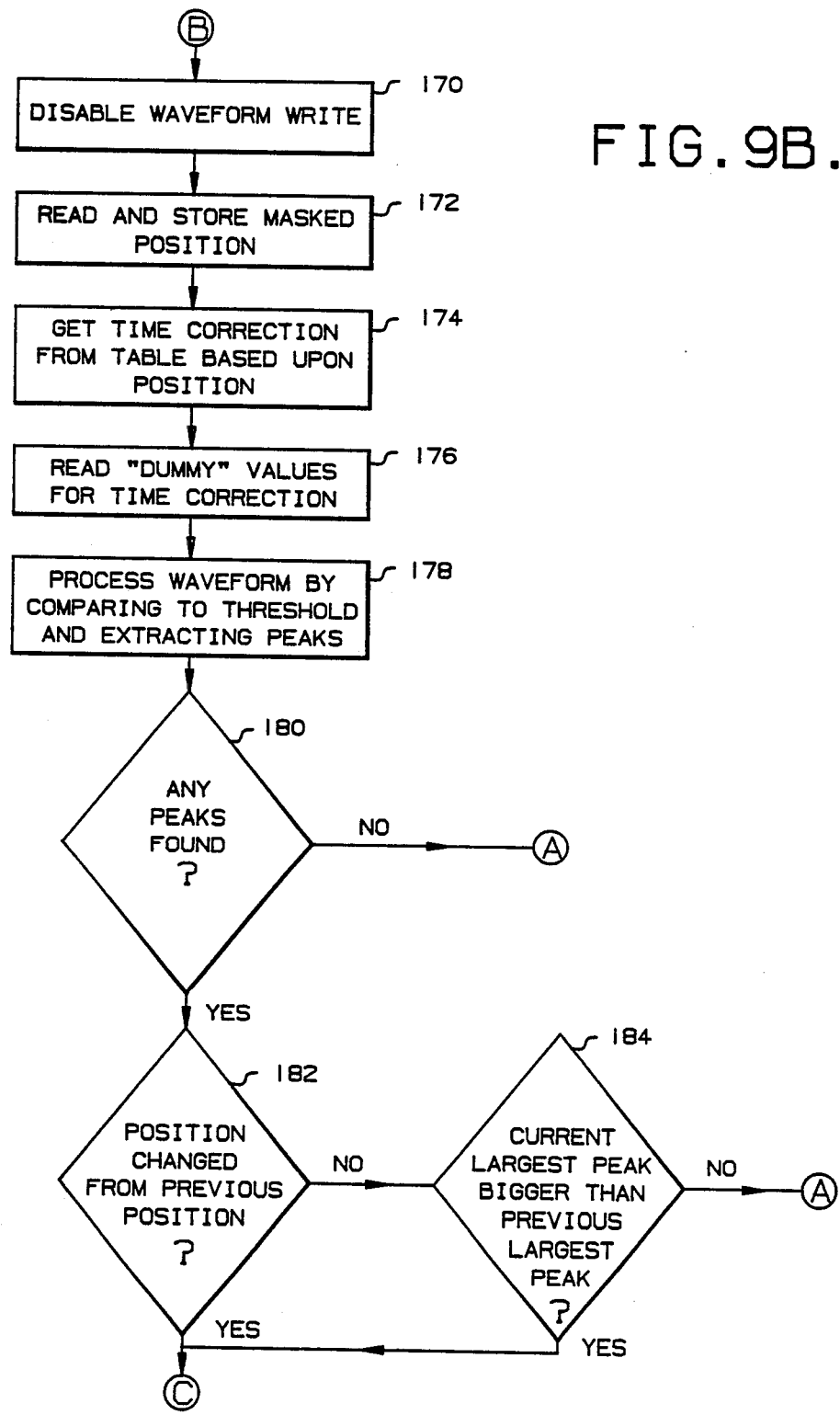
Figure 9C:
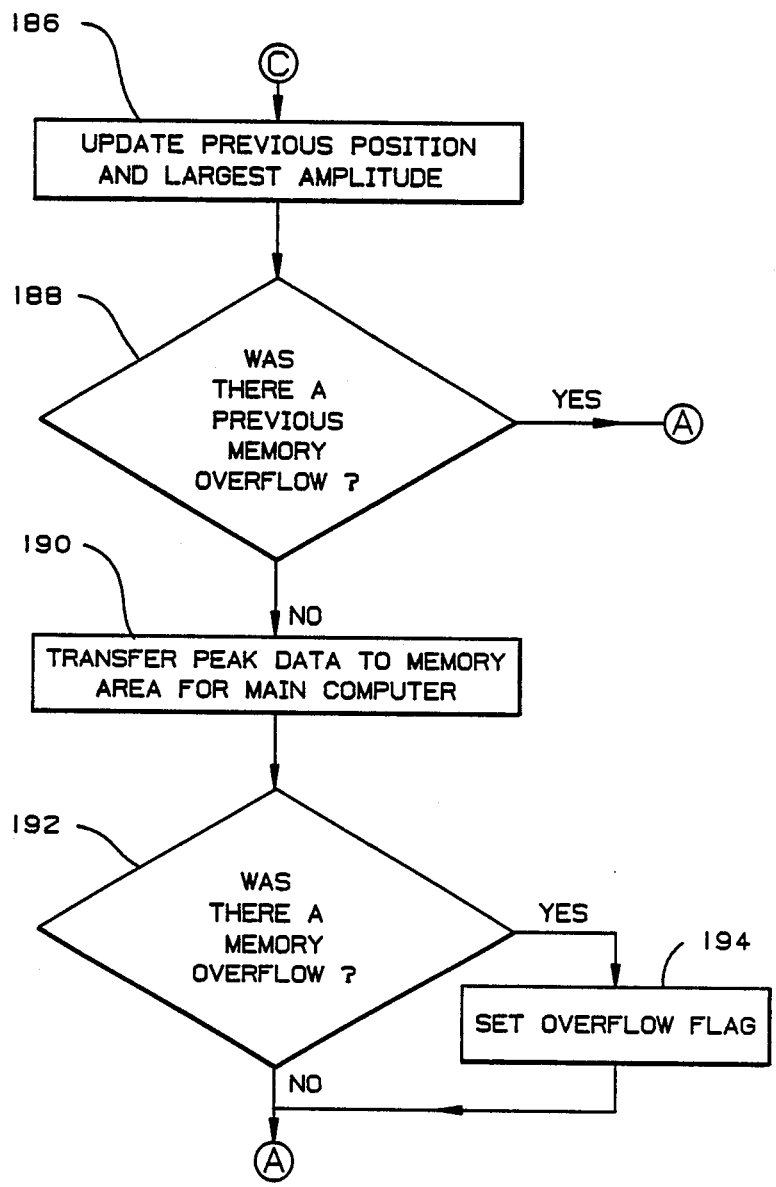

The procedure performed by the CPU 120 of each flaw gate, as illustrated in FIG. 6, is depicted by FIGS. 9A-9C. This figure does not show the procedure executed by the main control computer 10 which initializes or sets up the flaw gate. The control computer 10 in the set up procedure, prior to processing by the flaw gate, loads the following variable information into the variable portion of memory 122 by taking control of the address 124 and data bus 126 as previously discussed: the channel number which selects the time window during which the flaw gate should record samples; the number of peaks N indicating the number of excursions of the return signal waveform above the threshold curve in addlition to the maximum amplitude indication which should be stored for transfer to control computer 10; the length of the threshold curve which controls the number of comparisons necessary for indication processing; the threshold curve data values; a 16 bit position mask which masks out the unused bit positions on the data and control bus for the 14 bit resolver position from the resolver 24; an optional 16 bit start position mask which can be used to activate the flaw gate based on a coarse circumferential position of the transducer, if desired; and a ranging curve which preferably includes 256 values for the 360° of a circumferential scan thereby providing ranging time corrections at a resolution of 1.4° even though the angular resolution of the system is 0.02°.

At the start of the procedure (FIG. 9A), a determination is made 152 concerning whether the flaw gate should be in a digitizing mode 154 by examining memory 122 to see if a digitizing command from control computer 10 is resident therein. In the digitizing mode the flaw gate merely samples from waveform memory 134 and stores the samples in memory 122 and does not process same using the threshold waveform, thereby allowing the control computer 10 to retrieve actual amplitude signals. The digitizing mode is used, for example, to record actual amplitude signals from calibration reflectors or flaws as desired by the operator for archival purposes.

If the digitizing mode command is not resident in the variable portion of memory 122, the flaw gate processor 120 sends 156 a status word to the control computer 10 indicating that the flaw gate is operating in the flaw gate mode. The processor then obtains 160 the start position and start position mask from the variable portion of memory 122 and begins comparing 162 the start positions (angles) with the position produced by the resolver and stored in position latch 118. If starting at an optional start position is not desired, then the position mask would be all zeros.

When the start position is reached the channel code is read 164 from memory 122 and stored 166 in channel latch 112 to allow waveform memory 116 to be activated when the channel code from the timing control unit 26 matches the contents of latch 112. The processing unit 120 then monitors the output of comparator 114 which indicates when the window has been opened and then closed, indicating that a waveform has been stored. When a waveform has been stored in waveform memory unit 116 the write mode of the memory unit 116 is disabled 170 (FIG. 9B). Next, the resolver position is read and stored 172 in the portion of the memory 122 which will be transferred to the control computer 10 and indicates the current position or angle of the transducer 20 from which the indication was obtained. The time correction from the ranging curve for the current position is retrieved 174 and used, after the memory address has been reset, to read and discard 176 the dummy values from the waveform memory 116 until the return sample waveform is shifted to the appropriate start position for threshold comparison.

Next, the CPU 120 processes 178 the return signal waveform as previously discussed by comparing the waveform to the threshold curve 136 and extracting the excursion information to obtain indications. If peaks are found 180, a comparison is made 182 with the previous resolver position so that the storage of duplicate reflector indications can be prevented when the position has not changed. If, however, the amplitude of the largest peak has increased, even though transducer position has not changed, the value of the previous largest peak along with the previous position are updated 186 (FIG. 9C) and the previous set of indications are replaced by the current.

If a previous memory overflow has not occurred 188, as determined by examining an overflow flag, the peak data is transferred 190 to the portion of the memory 122 accessible by control computer 10. If there has been a memory overflow, that is, the available memory in which reflection indications can be stored is full the overflow flag in memory 122 is set 194. The overflow flag allows control computer 10 to determine that an overflow has occurred and immediately retrieve the reflector indication data and start a rescan from the last position recorded in memory 122 if desired. Once all of the data has been processed, the flaw gate repeats the procedure by getting 164 the channel code from memory 122, storing 166 the channel code in the latch, and monitoring 168 the output of comparator 114 until a waveform is written.

Figure 11:
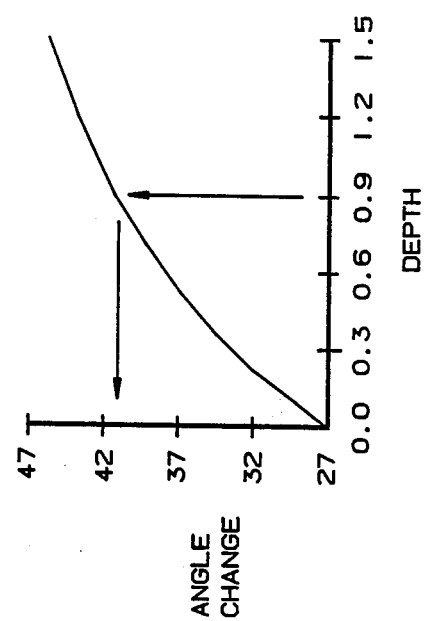
FIGS. 10 and 11 illustrate how a flaw is located based on the indication data provided by the flaw gate.
Figure 10:
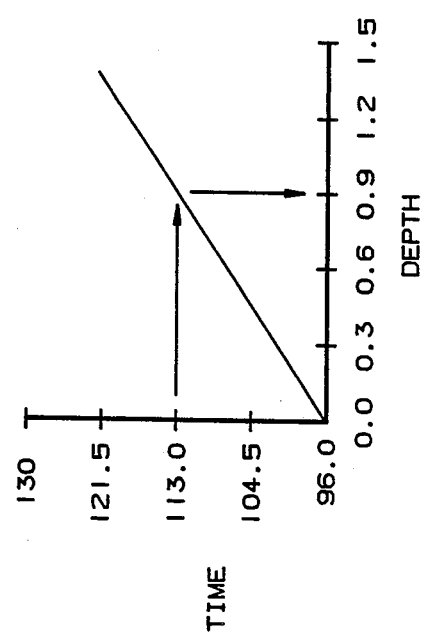

FIGS. 10 and 11 indicate how the peak time of each indication of the largest peak above the threshold can be used by the control computer 10 to obtain the depth and modify the angle of the indication. The time versus depth curve of FIG. 10 can be produced during calibration using known position reflectors or calculated from the known velocity of sound in the material being examined. Because the actual angle of the indication with respect to depth differs from the transducer angular position in a non-linear manner due to the geometry of the beam path, the depth, determined from the peak time using the curve of FIG. 10, is then used in the curve of FIG. 11 to obtain an angle change which corrects the transducer angle (position) and the angle of refraction of the beam in the material to pinpoint the exact angle of the indication. The geometry of the beam in the immersion fluid and the material being inspected, is discussed in detail in the related applications. The depth versus angle change curve of FIG. 11 can also be determined during calibration or calculated from the known characteristics of sound travel in the material being examined. In actual practice, the curves of FIGS. 10 and 11 are represented by equations derived from the beam path geometry as determined during calibration. The corrected angle is added to a fixed offset angle, which is an offset from a reference position, to obtain an adjusted or referenced indication angle. The depth and adjusted flaw angle define the location of the indication along with the axial (Z) position of the transducer. The depth, angle and axial position can then be used to display flaw indications using a known display system which allows the image of the object being inspected to be presented in several different views along with the detected indications in order to see the location and size of flaws.

The many features and advantages of the invention are apparent from the detailed specification and thus it is intended by the appended claims to cover all such features and advantages of the invention which fall within the true spirit and scope thereof. Further, since numerous modifications and changes will readily occur to those skilled in the art, it is not desired to limit the invention to the exact construction and operation illustrated and described, and accordingly all suitable modifications and equivalents may be resorted to, falling within the scope of the invention. For example, the discussion herein has assumed that the reflections, for a single beam pulse focused at a particular depth, are processed during transit time windows that correspond to depth. This introduces inaccuracies in flaw location determinations because the beam is not completely in focus at depths other than the geometric focus depth. Since the array transducer can be focused for the highest beam precision at any desired depth, for higher accuracy, it is possible to focus the beam at the center of a particular depth/time window and only open that window for flaw processing. Additional pulses can be produced and focused for other depth/time windows. The windows can then be made arbitrarily large or small depending on the resolution of flaw location desired. An improvement in the speed of the comparison process can be accomplished if the address counter 132 in the waveform memory unit can be loaded with an address offset which compensates for ranging changes rather than simply incrementing the counter to produce the offset. It is also possible to compare return signal waveform points with an offset threshold as the data arrives if a very high speed processor is substituted for the preferred Z80. This very high speed processor would have to have an instruction cycle time at least several times as fast as the 20 MHz data rate. Another modification is for the flaw gates 36–42 to have available on the control and data bus 30 additional test parameters such as temperature and time of day, and then for the flaw gate to read and store these additional parameters, as well as or instead of, the position of the transducer.

What is claimed is:

1. An ultrasonic signal processing system for an ultrasonic transducer, comprising:
   transducer control and signal digitizing means for controlling transmit signal production, digitizing reflection signals and indicating transducer position; and
   flaw indication processing means for storing the digitized reflection signals as a reflection waveform, comparing the reflection waveform to a threshold waveform, producing and storing flaw indications when the reflection waveform exceeds the threshold waveform, and storing the transducer position in association with the flaw indications.

2. An ultrasonic signal processing system for an ultrasonic transducer, comprising:
   transducer control and signal digitizing means for controlling transmit signal production, digitizing reflection signals and indicating transducer position; and
   flaw indication processing means for storing the digitized reflection signals as a reflection waveform, comparing the reflection waveform to a threshold waveform, producing and storing flaw indications when the reflection waveform exceeds the threshold waveform, storing the transducer position in association with the flaw indications, storing a transit time offset curve including a ranging offset and adjusting the start of the threshold waveform comparison before comparison by the ranging offset that is a function of transducer position.

3. An ultrasonic signal processing system for an ultrasonic transducer, comprising:
   transducer control and signal digitizing means for controlling transmit signal production, digitizing reflection signals, indicating transducer position, and producing a window indicator designating a window during which said flaw indication processing means is to be activated; and
   flaw indication processing means for storing the digitized reflection signals as a reflection waveform, comparing the reflection waveform to a threshold waveform, producing and storing flaw indications when the reflection waveform exceeds the threshold waveform, and storing the transducer position in association with the flaw indications, said flaw indication processing means comprising:
   waveform window detection means for detecting the window indicator;
   a waveform memory unit operatively connected to said transducer control and signal digitizing means and said waveform window detection means, and storing the digitized reflection signals during the window;
   a position latch operatively connected to said transducer control and signal digitizing means and storing the transducer position;
   a storage memory storing the threshold waveform, the flaw indications and the position;
   a processor, operatively connected to said waveform detection means, said waveform memory unit, said position latch and said storage memory, performing the comparison and storing the flaw indications in said storage memory.

4. A system as recited in claim 3, wherein said window is a time/depth window.

5. A system as recited in claim 3, wherein said waveform window detection means comprises:
   a channel latch, operatively connected to said processor and loaded with a channel code by said processor; and
   a comparator operatively connected to said channel latch and to said transducer control and signal digitizing means, and comparing the window indicator to the channel code and activating said waveform memory unit when coincidence occurs.

6. A system as recited in claim 5, wherein said transducer control and signal digitizing means produces a write signal when a reflection signal sample is available for storage and said waveform memory unit comprises:
   a waveform memory operatively connected to said transducer control and signal digitizing means and storing the reflection signal sample when the write signal is received; and
   an address counter operatively connected to said waveform memory, said comparator and said transducer control and signal digitizing means, designating the location at which the reflection signal sample is stored and being incremented by the write signal in accordance with the activation by said comparator.

7. A system as recited in claim 3, further comprising:
   data access means, operatively connected to said processor and said storage memory, for disabling said processor and retrieving the reflector indications and the position from said storage memory.

8. An ultrasonic signal processing system, comprising:
   a control processor;
   a timing control unit connected to said control processor and producing timing control signals including window signals;
   a pulse control unit connected to and controlled by said timing control unit;

an inspection transducer connected to and controlled by said pulse control unit and producing a received signal;

a resolver coupled to said inspection transducer and producing a position of said inspection transducer;

an analog multiplexer connected to said timing control unit and said inspection transducer, and attenuating the received signal in dependence on the window signals;

a digitizer connected to said analog multiplexer and digitizing the attenuated received signal; and plural flaw gates, connected to said digitizer, said timing control unit and said resolver, each storing and processing, in dependence on one of the window signals, the digitized attenuated received signals by shifting a threshold waveform in dependence on a ranging offset and comparing the stored digitized attenuated received signals to the shifted threshold waveform and producing flaw indications when the digitized received signals exceed the threshold waveform, and storing the position, said control processor retrieving the flaw indications and corresponding position at the end of a scan by said inspection transducer and determining flaw locations from the positions and flaw indications.

9. A method of processing transducer signals to determine flaw indications, said method comprising the steps of:

(a) storing the transducer signals as a sample waveform;

(b) shifting a threshold waveform in dependence on a ranging offset; and (c) comparing the threshold and sample waveforms and storing peak amplitude and peak amplitude time of excursions of the sample waveform above the threshold waveform as flaw indications.

10. A method as recited in claim 9, wherein step (a) is performed during a time window corresponding to the depth of the indications.

11. A method as recited in claim 9, wherein step (c) includes storing a rising crossing time of the excursion and a falling crossing time of the excursion.

12. A method of determining flaw indications in a material being inspected using an inspection transducer and a ranging transducer, comprising the steps of:

(a) obtaining a ranging offset of the material from the ranging transducer at a position;

(b) activating the inspection transducer to produce an inspection signal at the position;

(c) sampling the returned inspection signal during a sample window to produce a digital return signal sample waveform;

(d) shifting a digital return signal sample waveform using the ranging offset;

(e) comparing a threshold waveform to the shifted return signal sample waveform;

(f) storing the peak amplitude and peak time of excursions of the shifted return signal sample waveform above the threshold waveform;

(g) repeating steps (b)-(f) at different positions; and (h) transferring the peak amplitudes, peak times and positions to a flaw location determination device.

13. An ultrasonic signal processing system for an ultrasonic transducer, comprising:

transducer control and signal digitizing means for controlling transmit signal production, digitizing reflection signals and indicating transducer position; and flaw indication processing means for storing the digitized reflection signals as a reflection waveform, comparing the reflection waveform to a threshold waveform, and producing and storing flaw indications when the reflection waveform exceeds the threshold waveform.

* * * * *